(12) United States Patent
Scherer et al.

(10) Patent No.: US 12,128,010 B2
(45) Date of Patent: *Oct. 29, 2024

(54) SEMIFLUORINATED COMPOUNDS AND THEIR COMPOSITIONS

(71) Applicant: NOVALIQ GMBH, Heidelberg (DE)

(72) Inventors: Dieter Scherer, Laufen (CH); Ralf Grillenberger, Nuremberg (DE); Frank Löscher, Schriesheim (DE); Hartmut Voss, Schriesheim (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,836

(22) Filed: Jun. 6, 2022

(65) Prior Publication Data

US 2022/0370377 A1 Nov. 24, 2022

Related U.S. Application Data (60) Continuation of application No. 16/874,617, filed on May 14, 2020, now Pat. No. 11,357,738, which is a division of application No. 16/180,994, filed on Nov. 5, 2018, now Pat. No. 10,682,315, which is a continuation of application No. 15/280,306, filed on Sep. 29, 2016, now abandoned.

(30) Foreign Application Priority Data

Sep. 30, 2015 (EP) .................................... 15187767
Oct. 30, 2015 (EP) .................................... 15192441

(51) Int. Cl.
| | | |
|---|---|---|
| *A61K 31/02* | (2006.01) | |
| *A61F 9/00* | (2006.01) | |
| *A61K 9/00* | (2006.01) | |
| *A61K 9/08* | (2006.01) | |
| *A61P 27/02* | (2006.01) | |

(52) U.S. Cl.
CPC ............ *A61K 31/02* (2013.01); *A61F 9/0008* (2013.01); *A61K 9/0048* (2013.01); *A61K 9/08* (2013.01); *A61P 27/02* (2018.01)

(58) Field of Classification Search
CPC ........ A61K 31/02; A61K 9/0048; A61K 9/08; A61F 9/0008; A61P 27/02
See application file for complete search history.

(56) References Cited

U.S. PATENT DOCUMENTS

| | | |
|---|---|---|
| 2,616,927 A | 11/1952 | Kauck et al. |
| 4,452,818 A | 6/1984 | Haidt |
| 4,649,047 A | 3/1987 | Kaswan |
| 5,077,036 A | 12/1991 | Long, Jr. |
| 5,126,127 A | 6/1992 | Bhagwat et al. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,340,567 A | 8/1994 | Cole et al. |
| 5,370,313 A | 12/1994 | Beard |
| 5,518,731 A | 5/1996 | Meadows |
| 5,578,020 A | 11/1996 | Mosley |
| 5,667,809 A | 9/1997 | Trevino |
| 5,849,291 A | 12/1998 | Kessler |
| 5,851,544 A | 12/1998 | Penska et al. |
| 5,874,469 A | 2/1999 | Maniar et al. |
| 5,874,481 A | 2/1999 | Weers |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,105 B1 | 7/2001 | Johnstone |
| 6,262,126 B1 | 7/2001 | Meinert |
| 6,264,990 B1 | 7/2001 | Knepp et al. |
| 6,294,563 B1 | 9/2001 | Garst |
| 6,335,335 B2 | 1/2002 | Higashiyama et al. |
| 6,372,243 B2 | 4/2002 | Kobuch et al. |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,576,663 B2 | 6/2003 | Klimko |
| 6,730,328 B2 | 5/2004 | Maskiewicz |
| 7,001,607 B1 | 2/2006 | Menz |
| 7,026,359 B1 | 4/2006 | Gross |
| 7,041,705 B2 | 5/2006 | Mishra et al. |
| 7,063,241 B2 | 6/2006 | Spada et al. |
| 7,074,827 B2 | 7/2006 | Ueno |
| 7,258,869 B1 | 8/2007 | Berry |
| 7,283,239 B2 | 10/2007 | Nonogaki et al. |
| 7,608,261 B2 | 10/2009 | Furfine et al. |
| 7,687,455 B2 | 3/2010 | Bonnet et al. |
| 7,740,875 B2 | 6/2010 | Dechow |
| 7,776,349 B2 | 8/2010 | Dechow |

(Continued)

FOREIGN PATENT DOCUMENTS

| | | |
|---|---|---|
| AT | 509000 A1 | 5/2011 |
| CA | 2481394 A1 | 12/2003 |

(Continued)

OTHER PUBLICATIONS

Qiao et al. "Emerging treatment options for meibomian gland dysfunction," Clinical Ophthalmology, 2013:7, 1797-1803 (Year: 2013).*

(Continued)

*Primary Examiner* — Noble E Jarrell
*Assistant Examiner* — Richard Grant Peckham
(74) *Attorney, Agent, or Firm* — Hoxie & Associates LLC (57) ABSTRACT

The present invention is directed to compositions comprising semifluorinated compounds and their use as medicaments for topical administration to the eye.

13 Claims, 2 Drawing Sheets

(56) References Cited

U.S. PATENT DOCUMENTS

| | | |
|---|---|---|
| 8,029,977 B2 | 10/2011 | Meinert et al. |
| 8,222,292 B2 | 7/2012 | Goskonda et al. |
| 8,328,775 B2 | 12/2012 | Gokhale et al. |
| 8,343,945 B2 | 1/2013 | Tamarkin et al. |
| 8,470,873 B2 | 6/2013 | Chen |
| 8,492,334 B2 | 7/2013 | Lavik et al. |
| 8,501,800 B2 | 8/2013 | Bowman et al. |
| 8,614,178 B2 | 12/2013 | Theisinger et al. |
| 8,759,281 B2 | 6/2014 | Bonnet et al. |
| 8,759,404 B2 | 6/2014 | Daftary et al. |
| 8,772,337 B2 | 7/2014 | Pilotaz et al. |
| 8,796,340 B2 | 8/2014 | Theisinger et al. |
| 8,865,131 B2 | 10/2014 | Hagedorn et al. |
| 8,916,157 B2 | 12/2014 | Krause et al. |
| 8,986,738 B2 | 3/2015 | Meinert |
| 9,000,048 B2 | 4/2015 | Mecozzi et al. |
| 9,005,626 B2 | 4/2015 | Seigfried |
| 9,023,898 B2 | 5/2015 | Wong et al. |
| 9,186,305 B1 | 11/2015 | Suzuki |
| 9,241,900 B2 | 1/2016 | Wilson |
| 9,265,809 B2 | 2/2016 | Johnson |
| 9,278,120 B2 | 3/2016 | Cruzat et al. |
| 9,308,262 B2 | 4/2016 | Wilson |
| 9,446,026 B2 | 9/2016 | Bingaman et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 9,878,000 B2 | 1/2018 | Gu et al. |
| 9,968,678 B2 | 5/2018 | Theisinger et al. |
| 10,045,996 B2 | 8/2018 | Theisinger et al. |
| 10,045,997 B2 | 8/2018 | Chen et al. |
| 10,058,615 B2 | 8/2018 | Günther et al. |
| 10,064,944 B2 | 9/2018 | Wilson |
| 10,123,904 B2 | 11/2018 | Chauhan et al. |
| 10,130,707 B2 | 11/2018 | Günther et al. |
| 10,273,298 B2 | 4/2019 | Günther et al. |
| 10,286,035 B2 | 5/2019 | Gavaris |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 * | 6/2020 | Scherer ................. A61F 9/0008 |
| 10,813,976 B2 | 10/2020 | Loscher et al. |
| 10,813,999 B2 | 10/2020 | Günther et al. |
| 11,154,513 B2 * | 10/2021 | Scherer ................... A61P 27/02 |
| 11,160,865 B2 | 11/2021 | Theisinger et al. |
| 11,241,497 B2 | 2/2022 | Reza et al. |
| 11,273,174 B2 | 3/2022 | Löscher et al. |
| 11,278,503 B2 | 3/2022 | Günther et al. |
| 11,285,163 B2 | 3/2022 | Shah et al. |
| 11,324,757 B2 | 5/2022 | Theisinger et al. |
| 11,357,738 B2 * | 6/2022 | Scherer ................. A61F 9/0008 |
| 11,400,132 B2 | 8/2022 | Loscher et al. |
| 11,413,323 B2 | 8/2022 | Leo et al. |
| 11,457,626 B2 | 10/2022 | Dyer |
| 11,576,893 B2 | 2/2023 | Löscher et al. |
| 11,583,513 B2 | 2/2023 | Günther et al. |
| 11,684,589 B2 | 6/2023 | Günther et al. |
| 11,723,861 B2 | 8/2023 | Günther et al. |
| 11,730,794 B2 | 8/2023 | Yancopoulos |
| 11,844,836 B2 | 12/2023 | Günther et al. |
| 11,896,559 B2 | 2/2024 | Günther et al. |
| 11,987,623 B2 | 5/2024 | Günther et al. |
| 12,005,033 B2 | 6/2024 | Günther et al. |
| 2002/0004063 A1 | 1/2002 | Zhang |
| 2002/0006442 A1 | 1/2002 | Mishra et al. |
| 2002/0128527 A1 | 9/2002 | Meinert |
| 2002/0137793 A1 | 9/2002 | Klimko |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson |
| 2005/0075407 A1 | 4/2005 | Tamarkin et al. |
| 2005/0079210 A1 | 4/2005 | Gupta |
| 2005/0084553 A1 | 4/2005 | Moon et al. |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0009522 A1 | 1/2006 | Reza et al. |
| 2006/0078580 A1 | 4/2006 | Dechow |
| 2006/0153905 A1 | 7/2006 | Carrara et al. |
| 2007/0238732 A1 | 10/2007 | Graham et al. |
| 2008/0019926 A1 | 1/2008 | Krafft et al. |
| 2008/0039807 A1 | 2/2008 | Pine |
| 2008/0050335 A1 | 2/2008 | Faour et al. |
| 2008/0089923 A1 | 4/2008 | Burkstrand et al. |
| 2008/0112895 A1 | 5/2008 | Kottayil et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0254106 A1 | 10/2008 | Bell |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2009/0226875 A1 | 9/2009 | Meinert et al. |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0137252 A1 | 6/2010 | Matsumura et al. |
| 2010/0189765 A1 | 7/2010 | Erickson et al. |
| 2010/0226997 A1 | 9/2010 | Bowman et al. |
| 2010/0274215 A1 | 10/2010 | Wong et al. |
| 2010/0305081 A1 | 12/2010 | Dechow |
| 2010/0310476 A1 | 12/2010 | Tamarkin et al. |
| 2011/0223208 A1 | 9/2011 | Hill et al. |
| 2011/0269704 A1 | 11/2011 | Seigfried |
| 2012/0010280 A1 | 1/2012 | Aleo et al. |
| 2012/0053242 A1 | 3/2012 | Cela Lopez |
| 2012/0095097 A1 | 4/2012 | Tabuchi et al. |
| 2012/0100183 A1 | 4/2012 | Schlessinger et al. |
| 2012/0219640 A1 | 8/2012 | Wright |
| 2012/0238639 A1 | 9/2012 | Theisinger et al. |
| 2012/0244177 A1 | 9/2012 | Theisinger et al. |
| 2013/0011484 A1 | 1/2013 | Bevier |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0309226 A1 | 11/2013 | Armstrong et al. |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0155488 A1 | 6/2014 | Warner et al. |
| 2014/0186350 A1 | 7/2014 | Ghosh et al. |
| 2014/0303219 A1 | 10/2014 | Bingaman et al. |
| 2014/0369993 A1 | 12/2014 | Günther et al. |
| 2015/0045282 A1 | 2/2015 | Elsohly et al. |
| 2015/0099019 A1 | 4/2015 | Johnson |
| 2015/0174096 A1 | 6/2015 | Bottger et al. |
| 2015/0224064 A1 | 8/2015 | Günther et al. |
| 2015/0238605 A1 | 8/2015 | Günther et al. |
| 2015/0258040 A1 | 9/2015 | Lynch et al. |
| 2016/0000941 A1 | 1/2016 | Keller et al. |
| 2016/0101178 A1 | 4/2016 | Wilson |
| 2016/0159902 A1 | 6/2016 | Günther et al. |
| 2016/0184259 A1 | 6/2016 | Anastassov et al. |
| 2016/0243189 A1 | 8/2016 | Gu et al. |
| 2016/0303031 A1 | 10/2016 | El Achkar et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0216204 A1 | 8/2017 | Theisinger et al. |
| 2017/0348285 A1 | 12/2017 | Hellstrom |
| 2018/0360908 A1 | 12/2018 | Beier et al. |
| 2019/0000919 A1 | 1/2019 | Brockmeyer et al. |

(56) References Cited

U.S. PATENT DOCUMENTS

| | | |
|---|---|---|
| 2019/0125658 A1 | 5/2019 | Ficko |
| 2019/0256591 A1 | 8/2019 | Günther et al. |
| 2019/0298801 A1 | 10/2019 | Kerwin et al. |
| 2019/0328717 A1 | 10/2019 | Günther et al. |
| 2019/0343793 A1 | 11/2019 | Günther et al. |
| 2020/0060987 A1 | 2/2020 | Gunther et al. |
| 2020/0188318 A1 | 6/2020 | Günther et al. |
| 2021/0069014 A1 | 3/2021 | Löscher et al. |
| 2021/0121471 A1 | 4/2021 | Löscher et al. |
| 2021/0228595 A1 | 7/2021 | Löscher et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |
| 2022/0143137 A1 | 5/2022 | Witt et al. |
| 2022/0152096 A1 | 5/2022 | Loscher et al. |
| 2022/0226427 A1 | 7/2022 | Leo et al. |
| 2022/0354786 A1 | 11/2022 | Friess et al. |
| 2022/0354926 A1 | 11/2022 | Loscher et al. |
| 2022/0362382 A1 | 11/2022 | Loscher et al. |
| 2023/0043641 A1 | 2/2023 | Beier et al. |
| 2023/0181679 A1 | 6/2023 | Haisser et al. |
| 2023/0330056 A1 | 10/2023 | Günther et al. |
| 2023/0398065 A1 | 12/2023 | Günther et al. |

FOREIGN PATENT DOCUMENTS

| | | |
|---|---|---|
| CN | 200977281 Y | 11/2007 |
| CN | 202136470 U | 2/2012 |
| CN | 203524843 U | 4/2014 |
| CN | 106176937 A | 12/2016 |
| EP | 0 593 552 | 4/1994 |
| EP | 0 670 159 | 9/1995 |
| EP | 1 152 749 | 11/2001 |
| EP | 2 802 331 A1 | 7/2013 |
| EP | 2 708 228 | 3/2014 |
| EP | 2 730 291 A1 | 5/2014 |
| JP | S5721312 A | 2/1982 |
| JP | S6452722 | 2/1989 |
| JP | H0764702 B2 | 7/1995 |
| JP | 2001/158734 | 6/2001 |
| JP | 2011/006348 | 1/2011 |
| JP | 2011/024841 A | 2/2011 |
| RU | 2 111 738 C1 | 5/1998 |
| WO | WO-93/000991 A1 | 1/1993 |
| WO | WO 98/05301 | 12/1998 |
| WO | WO 00/054588 | 9/2000 |
| WO | WO 2003/099258 | 12/2003 |
| WO | WO 2005/099752 | 10/2005 |
| WO | WO 2005/123035 | 12/2005 |
| WO | WO 2006/042059 | 4/2006 |
| WO | WO 2006/048242 | 5/2006 |
| WO | WO 2007/008666 | 1/2007 |
| WO | WO 2007/052288 | 5/2007 |
| WO | WO 2008/019146 | 2/2008 |
| WO | WO 2008/060359 | 5/2008 |
| WO | WO-2008/136034 A2 | 11/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO-2012/007776 A2 | 1/2012 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |
| WO | WO 2015/011199 | 1/2015 |
| WO | WO 2015/053829 | 4/2015 |
| WO | WO 2015/074137 | 5/2015 |
| WO | WO 2016/025560 | 2/2016 |
| WO | WO-2016/082644 | 6/2016 |
| WO | WO-2016/108130 | 7/2016 |
| WO | WO 2016/109531 | 7/2016 |
| WO | WO-2017/120601 A1 | 7/2017 |
| WO | WO 2017/220625 | 12/2017 |
| WO | WO 2018/054932 | 3/2018 |
| WO | WO 2018/055101 | 3/2018 |
| WO | WO 2018/060282 | 4/2018 |
| WO | WO 2018/114557 | 6/2018 |
| WO | WO 2018/115097 | 6/2018 |

OTHER PUBLICATIONS

Ahmed, et al., "Disposition of Timolol and Inulin in the Rabbit Eye Following Corneal Versus Non-Corneal Absorption," International Journal of Pharmaceutics, 1987, 38:9-21.

Baerdemaeker, "Pharmacokinetics in Obese Patients," Continuing Education in Anesthesia, Critical Care & Pain, 2004, 4:152-155.

Barata-Vallejo et al., "(Me$_3$Si)$_3$SiH-Mediated Intermolecular Radical Perfluoroalkylation Reactions of Olefins in Water," J. Org. Chem., 2010, 75:6141-6148.

Bardin et al., "Long-Range Nanometer-Scale Organization of Semifluorinated Alkane Monolayers at the Air/Water Interface," Langmuir, 2011, 27:13497-13505.

Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.

Blackie et al., "MGD: Getting to the Root Cause of Dry Eye", Review of Optometry, 2012, pp. 1-12.

Broniatowski, M. et al., "Langmuir Monolayers Characteristics of Perfluorodecyl)-Alkanes," Journal of Physical Chemistry B, 2004, 108:13403-13411.

Chemical Book, "5-Fluorouracil," available at http://www.chemicalbook.com/-ChemicalProductProperty_EN_CB8162744.htm>, accessed Mar. 7, 2014.

Chhadva et al., "Meibomian Gland Disease The Role of Gland Dysfunction in Dry Eye Disease," Ophthalmology (2017) 124(11 Supplement): S20-S26.

Costa Gomes et al., "Solubility of dioxygen in seven fluorinated liquids," Journal of Fluorine Chemistry, 2004, 125, 1325-1329.

Davies, "Biopharmaceutical Considerations in Topical Ocular Drug Delivery," Clin. Exper. Pharmacol. Physiol., 2000, 27:558-562.

Dembinski et al., Semi-fluorinated Alkanes as Carriers for Drug Targeting in Acute Respiratory Failure, Experimental Lung Research, 2010, 36(8):499-507.

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, 2004.

Dias et al., "Solubility of oxygen in liquid perfluorocarbons," Fluid Phase Equilibria, 2004, 222-223:325-330.

Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).

English-language machine translation of EP0670159 (A1) issued in U.S. Appl. No. 14/122,025, filed Apr. 1, 2015, 10 pages.

"EvoTears—Gebrauchsanweisung," May 2015, retrieved from the Internet, date retrieved: Jun. 26, 2018, 2 pages, URL: http://video.apo-rot.de/docs/11213615.pdf.

Fischer, K.M., et al., "Effects of a topically applied 2% delta-9-tetrahydrocannabinol ophthalmic solution on intraocular pressure and aqueous humor flow rate in clinically normal dogs," American Journal of Veterinary Research, 2013, 74(2):275-280, Abstract Only (2 pages).

(56) References Cited

OTHER PUBLICATIONS

Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Gayton, J., "Etiology, Prevalence, and Treatment of Dry Eye Disease," Clinical Ophthalmology, 2009, 3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
Gerdenitsch, "Emulsions—established and promising drug carriers for parenteral administration", retrieved from Internet, date accessed: Jun. 20, 2016, URL: <http:/ipimediaworld.com/wp-content/uploads/2012/05/Pages-from-IPI-Volume-2-Issue-1-11.pdf.>.
German, E.J., et al., "Reality of drop size from multi-dose eye drop bottles: is it cause for concern?" Eye, 1999, 13:93-100.
Gopal et al., "Use of intravitreal injection of triamcinolone acetonide in the treatment of age-related macular degeneration," Indian J Ophthalmol., 2007, 55(6):431-435, (8 pages).
Grotenhermen, F., "Cannabinoids for therapeutic use—Designing systems to increase efficacy and reliability," American Journal of Drug Delivery, 2004, 2(4):229-240, Abstract Only (19 pages).
Hardung, H., "Semifluorierte und perfluorierte Vergindungen zur topischen und parenteralen Anwendung," 2008, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: An Experimental Study," Graefe's Archive for Clinical And Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
Ishizaki et al., "Treatment of Diabetic Retinopathy", Forum: Complication, Practice, 2009, 26(5): 474-476 (3 pages).
Joussen et al., "The concept of heavy tamponades—chances and limitations," Graefes Arch Exp Ophthalmol, 2008, 246:1217-1224.
Jonas et al., "Intravitreal triamcinolone acetonide for exudative age-related macular degeneration," Br J Ophthalmol, 2003, 87:462-468.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., Management of Dry Eye Disease, The American Journal of Managed Care, 2008, 14 (3):S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4):1873-1883.
Mantle et al., "Adverse and beneficial effects of plant extracts on skin and skin disorders," Adverse Drug Reaction and Toxicological Reviews, 2001, 20(2): 89-103.
Matteucci et al., "Biocompatibility assessment of liquid artificial vitreous replacements: relevance of in vitro studies," Survey of Ophthalmology, 2007, 52(3):289-299, Abstract Only (1 page).
Meinert et al., Biomaterials, Artificial Cells, and Immobilization Biotechnology, 1993, 21(5):583-95.
Meinert, H. et al., "Semifluorinated Alkanes—A New Class of Compounds with Outstanding Properties for Use in Ophthalmology," European Journal of Ophthalmology, 2000, 10 (3), 189-197.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Messmer, E.M., "The Pathophysiology, Diagnosis, and Treatment of Dry Eye Disease," (2015) Deutsches Arzteblatt International, 112(5):71-82.
Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.
O'Rourke, M. et al., "Enhancing Delivery of Topical Ocular Drops," Cataract & Refractive Surgery Today Europe, 2016, 2 pages.
Perry, "Dry Eye Disease: Pathophysiology, Classification, and Diagnosis," The American Journal of Managed Care, 2008, 14(3):S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome", Presented by Medical Online, New Ophthalmology, 1999, 16(7): 995-998 (4 pages).
Scherer et al., "Eyesol: A Novel Topical Ocular Drug Delivery System for Poorly Soluble Drugs," Drug Development & Delivery, vol. 13, No. 1, pp. 40-44, (2013).

(56) References Cited

OTHER PUBLICATIONS

Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Schnetler et al., "Lipid composition of human meibum: a review", S Afr Optom, 2013, 72(2), 86-93.
Spöler et al., ""Towards a New in vitro Model of Dry Eye: The ex vivo Eye Irritation Test"", Developments in Ophthalmology, 2010, 45, 93-107.
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.
Tiffany, J.M., "Individual Variations in Human Meibomian Composition", Exp. Eye Res., 1978, 27, 289-300.
Troiano et al., "Effect of Hypotonic .4% Hyaluronic Acid Drops in Dry Eye Patients: A Cross-Study", Cornea 27(10): 1126-1130 (Abstract Only).
"What is retinal vitrectomy?", Presented by: Medical Online, Obesity and Diabetes Mellitus, 2005, 4(2): 284-286 (3 pages).
Wang, W., "Lyophilization and Development of Solid Protein Pharmaceuticals," International Journal of Pharmaceutics, 2000, 203, 1-60.
Wirta, David L. et al., "A Clinical Phase II Study to Assess Efficacy, Safety and Tolerability of Waterfree Cyclosporine Formulation for the Treatment of Dry Eye Disease," Ophthalmology, 2019 126:792-800.
Wong et al., "Perfluorocarbons and Semifluorinated Alkanes," Seminars in Ophthalmology; vol. 15 (1), 2000, p. 25-35.
Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.
Xalatan, Latanoprost Ophthalmic Solution, 50 μg/mL Prostaglandin $F_{2\alpha}$analogue, Product Monograph, Jul. 21, 2014, 30 pages.
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).
Zhang et al., "Surface micelles of semifluorinated alkanes in Langmuir-Blodgett monolayers," Phys. Chem. Chem. Phys., 2004, 6:1566-1569.
"EvoTears, Product Description" Accessed Online: Dec. 21, 2023. https://evotears.com/at/das-produkt/ (Year: 2017).
"Highlights of Prescribing Information: Zioptan", pp. 1-11 (2014) https://www.accessdata.fda.gov/drugsatfda_docs/label/2015/202514s003s004lbl.pdf.
"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/news/home/20170105005211/en/Novaliq-Announces-Positive-Topline-Results-Phase-2>.
"Novaliq begins Phase 2 trial of Cyclasol for dry eye disease," Optometry Times, vol. 8, No. 3, (2016), p. 24.
"Ocular Surface Disease Index (OSDI)", Dec. 1, 2003, pp. 1-2, Retrieved from the Internet: URL: http://www.supereyecare.com/resources/OSDI.pdf.
"Xerophthalmia," Eye Clinic, 4 pages, archived Dec. 30, 2014.
"Zioptan Drug Label," Daily Med, NIH, (2017).
"Clascoterone (Winlevi®),"Chemical Abstracts, CAS Registry No. 19608-29-8, retrieved from the Internet, date accessed: Feb. 9, 2022, 3 pages URL:< https://www.chemicalbook.com/CASEN_19608-29-8.htm>.
"Semifluorinated alkane technology brings advantages for topical therapy," Ophthalmology Times, 2016, pp. 1-2.
Agarwal et al., "Modern Approaches to the Ocular Delivery of Cyclosporine A," Drug Discovery Today, vol. 21, No. 6, pp. 977-988, (2016); doi: 10.1016/j.drudis.2016.04.002.
Agarwal, R. et al., "Rodent Models of Experimental Autoimmune Uveitis," Methods Mol. Biol., vol. 900, pp. 443-469, (2012).
Agrahari, et al., "A comprehensive insight on ocular pharmacokinetics," Drug Delivery and Translational Research, vol. 6, No. 6, pp. 735-754, (2016).
Ahmed, S. et al., "Ocular Drug Delivery: a Comprehensive Review," AAPS PharmSciTech, vol. 24, No. 66, pp. 1-29, (2023).
Al-Amri, A. et al., "Long-term use of 0.003% tacrolimus suspension for treatment of vernal keratoconjunctivitis," Oman Journal of Ophthalmology, vol. 10, No. 3, pp. 145-149, (2017).
Ann Marie Griff, O.D., & Ann Pietrangelo, "Everything you need to know about keratoconjunctivitis," Healthline.com, Nov. 22, 2019, downloaded from https://www.healthline.com/health/keratoconjunctivitis.
Astellas Pharma US, Inc. (2019). PROGRAF(R); Highlights of Prescribing Information. Northbrook, IL: Astellas Pharma US, Inc.
AT509,000, Rausch Peter, "Water-soluble preparations of cannabinoids and cannabic preparations and their applications," May 15, 2011, English language machine translation, google patents, 1 page.
Babu, K. et al., "Medical Management of Uveitis—Current Trends," Indian J Opthalmol., vol. 61, No. 6, pp. 277-283, (2013).
Benezra, D. et al., "Cyclosporine eyedrops for the treatment of severe vernal keratoconjunctivitis," American Journal of Ophthalmology, vol. 101, pp. 278-282, (1986).
Bhargava, A. et al., "Ocular Allergic Disease," Drugs of Today/Medicamentos de Actualidad, J.R. Prous SS.A. International Publishers, vol. 34, No. 11, pp. 957-971, (1998).
Blume-Peytavi, U. et al., "A randomized double-blind placebo-controlled pilot study to assess the efficacy of a 24-week topical treatment by latanoprost 0.1% on hair growth and pigmentation in healthy volunteers with androgenetic alopecia," J Am Acad Dermatol, vol. 66, No. 5, pp. 794-800, (2012).
Bron, A. et al., "Grading of Corneal and Conjunctival Staining in the Context of Other Dry Eye Tests," Cornea, vol. 22, No. 7, pp. 640-650, (2003).
Cabral, T. et al., "Retinal and choroidal angiogenesis: a review of new targets," International Journal of Retina and Vitreous, vol. 3, No. 31, (2017).
Cequa® Prescribing Information, available at https://www.accessdata.fda.gov/drugsatfda_docs/label/2018/210913s000lbl.pdf (Aug. 2018) (last accessed Feb. 28, 2023).
Chaglasian, E. et al., "Recycling Cyclosporine," Review of Cornea & Contact Lenses, 2016, 5 pages.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chen, M. et al., "Persistent Inflammation Subverts Thrombospondin-1-Induced Regulation of Retinal Angiogenesis and is Driven by CCR2 Litigation," The American Journal of Pathology, vol. 180, pp. 235-245, (2012).
CN106176937A, Liu Yipeng, "Eczema-acne ointment," Dec. 7, 2016, English language machine translation of abstract, Espacenet, date obtained: Apr. 30, 2021, 1 page <https://worldwide.espacenet.com/patent/search/family/058089634/publication/CN106176937A?q=CN106176937A>.
Daull, P. et al., "Distribution of Cyclosporine A in Ocular Tissues After Topical Administration of Cyclosporine A Cationic Emulsions to Pigmented Rabbits," Cornea, vol. 32, No. 3, pp. 345-354, (2013), Abstract Only.

(56) References Cited

OTHER PUBLICATIONS

Dutescu, R. et al., "Semifluorinated alkanes as a liquid drug carrier system for topical ocular drug delivery," European Journal of Pharmaceutics and Biopharmaceutics, vol. 88, No. 1, pp. 123-128, (2014).
Elkeeb, R. et al., "Transungual Drug Delivery: Current Status," International Journal of Pharmaceutics, vol. 384, pp. 1-8, (2010).
Fraguas-Sanchez, A. et al., "Stability characteristics of cannabidiol for the design of pharmacological, biochemical and pharmaceutical studies," Journal of Chromatography B, (2020).
Galvao, J. et al., "Unexpected low-dose toxicity of the universal solvent DMSO," FASEB Journal, vol. 28, No. 3, pp. 1317-1330, (2014).
Garg, V. et al., "Topical tacrolimus nanoemulsion, a promising therapeutic approach for uveitis," Medical Hypotheses, vol. 81, pp. 901-904, (2013).
Goureau, O. et al., "Increased nitric oxide production in endotoxin-induced uveitis. Reduction of uveitis by an inhibitor of nitric oxide synthase," The Journal of Immunology, vol. 154, No. 12, pp. 6518-6523, (1995).
Griffin, W., "Classification of Surface-Active Agents by 'HLB'," Journal of the Society of Cosmetic Chemists, vol. 1, pp. 311-326, (1949).
Guirakhoo, F. et al., "Cloning, expression and functional activities of a single chain antibody fragment directed to fusion protein of respiratory syncytial virus," Immunotechnology, vol. 2, No. 3, pp. 219-228, (1996), Abstract Only.
Günther, B., "Breaking the Vicious Circle of Dry Eye Disease," OIS@ SECO, Feb. 21, 2019, pp. 1-14, New Orleans, URL: https://ois.net/wp-content/uploads/2019/02/DryEye-Novaliq.pdf.
He, F. et al., "High-throughput dynamic light scattering method for measuring viscosity of concentrated protein solutions" Analytical Biochemistry, vol. 399, No. 1, pp. 141-143, (2010), Abstract Only.
Ikervis® Prescribing Information, available at https://www.medicines.org.uk/emc/product/6937/smpc/print (Updated Mar. 2, 2022) (last accessed Apr. 27, 2023).
JPH0764702B2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.
JPS5721312a, Green Cross Corp, "Breathable Ointment," Apr. 2, 1982, English language machine translation of abstract, Espacenet, date obtained: Apr. 30, 2021, 1 page <https://worldwide.espacenet.com/patent/search/family/014132731/publication/JPS5721312A?q=JPS5721312A>.
Keratoconjunctivitis, Cleveland Clinic, last updated Jul. 8, 2022, downloaded from https://my.clevelandclinic.org/health/diseases/23551-keratoconjunctivitis.
Kerns et al., Drug-Like Properties: Concepts, Structure Design and Methods: from ADME to Toxicity Optimization, Elsevier, Chapter 10, Section 10.4.3, 133, (2008).
Kheirkhah, A. et al., "Topical 0.005% tacrolimus eye drop for refractory vernal keratoconjunctivitis," Eye (London, England), vol. 25, No. 7, pp. 872-880, (2011).
Kumar, S. et al., "Reduction in drop size of ophthalmic topical drop preparations and the impact of treatment," J. Adv. Pharm. Tech. Res., vol. 2, No. 3, (2011).
Lallemand et al., "Cyclosporine Delivery to the Eye: A comprehensive Review of Academic and Industrial Efforts," European Journal of Pharmaceutics and Biopharmaceutics, vol. 117, pp. 14-28, (2017).
Leonardi, A., "Allergy and allergic mediators in tears," Experimental Eye Research, vol. 117, pp. 106-117, (2013).
Li, Y. et al., "Limited Scleroderma (Crest Syndrome) is Associated with Worse Xerostomia and Xerophthalmia in Patients Being Evaluated for Primary Sjogren's Syndrome," Scientific Abstracts; FRI0432, pp. 583-584, (2015).
Li, Y. et al., "Limited Scleroderma (Crest Syndrome) is Associated with Worse Xerostomia and Xerophthalmia in Patients Being Evaluated for Primary Sjogren's Syndrome," Annals of Rheumatic Diseases, vol. 74, Supp. No. 2, Abstract FRI0432 (2015 Annual European Congress of Rheumatology), Jun. 12, 2015.
Martín-Montañez et al., "End-of-day dryness, corneal sensitivity and blink rate in contact lens wearers," Cont Lens Anterior Eye, vol. 38, No. 3, pp. 148-151, (2015).
Miller, K. et al., "Minimal Clinically Important Difference for the Ocular Surface Disease Index," Socioeconomics and Health Services, Arch Ophthalmol, vol. 128, No. 1, pp. 94-101, (2010).
Moscovici, B. et al., "Clinical treatment of dry eye using 0.03% tacrolimus eye drops," Cornea, vol. 31, No. 8, pp. 945-949, (2012).
Murdan, S., "Enhancing the Nail Permeability of Topically Applied Drugs," Expert Opinion on Drug Delivery, vol. 5, No. 11, pp. 1267-1282, (2008).
Murphy, C. et al., "Cyclosporine vs Tacrolimus Therapy for Posterior and Intermediate Uveitis," Arch Ophthalmol., vol. 123, pp. 634-641, (2005).
Neely, K. et al., "Ocular Neovascularization: Clarifying Complex Interactions," American Journal of Pathology, vol. 153, No. 3, (1998).
Ohashi, Y. et al., "A randomized, placebo-controlled clinical trial of tacrolimus ophthalmic suspension 0.1% in severe allergic conjunctivitis," Journal of ocular pharmacology and therapeutics, vol. 26, No. 2, pp. 165-174 (2010).
Ozcan, A. et al., "Management of Severe Allergic Conjunctivitis With Topical Cyclosporin A 0.05% Eyedrops," Cornea, vol. 26, No. 9, pp. 1035-1038, (2007).
Park, Y-R. et al., "Inhibitory Effect of Topical Aflibercept on Corneal Neovascularization in Rabbits," Cornea, vol. 34, No. 10, pp. 1303-1307, (2015).
Pinarci, E. et al., "Intraocular Gas Application in the Diagnosis and Treatment of Valsalva Retiopathy in Case with Premacular Hemorrhage," XP002625604, Retina-Vitreus, vol. 17, No. 2, pp. 153-155, (2009), Abstract only.
Prabhu, S. et al., "Topical Cyclosporine A 0.05% for Recurrent Anterior Uveitis," Br J Opthalmol, vol. 100, No. 3, pp. 345-347, (2016), Abstract Only.
Qiao, J. et al., "Emerging treatment options for meibomian gland dysfunction," Clinical Ophthalmology, vol. 7, pp. 1797-1803, (2013).
Restasis® Prescribing Information, available at https://www.accessdata.fda.gov/drugsatfda_docs/label/2012/050790s020lbl.pdf (Nov. 2012) (last accessed Feb. 28, 2023).
Rojas-Carabali, W. et al. "Clinical relationships between dry eye disease and uveitis: a scoping review," Journal of Ophthalmic Inflammation and Infection, vol. 13, No. 2, (2023).
Rosca-Casian, O. et al., "Antifungal Activity of Aloe vera Leaves," Fitoterapia, vol. 28, pp. 219-222, (2007).
Rosenbaum, J. et al., "Contrasting Ocular Effects of Local versus Systemic Endotoxin," Investigative Ophthalmology & Visual Science, vol. 52, No. 9, pp. 6472-6477, (2011).
Rosenberg, A., "Effects of Protein Aggregates: An Immunologic Perspective," The AAPS Journal, vol. 8, No. 3, pp. E501-E507, (2006).
RU2111738C1, Aktsionerone Obshchestvo Nizar, "Product to Enhance Sun-Protecting Activity of Photo-Protecting Agents," May 27, 1998, English language machine translation of abstract, Espacenet, date obtained: Apr. 30, 2021, 1 page <https://worldwide.espacenet.com/patent/search/family/020182059/publication/RU2111738C1?q=RU2111738C1>.
Sachdeva, S. "Hirsutism: Evaluation and Treatment," Indian J Dermatol, vol. 55, No. 1, pp. 3-7, (2010).
Sella, R. et al., "Efficacy of topical aflibercept versus topical bevacizumab for the prevention of corneal neovascularization in a rat model," Experimental Eye Research, vol. 146, pp. 224-232, (2016).
Sheppard, J. et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).
Singh, P. et al. "Pilosebaceous Unit: Anatomical Considerations and Drug Delivery Opportunities," Indian J of Pharmacol, vol. 32, pp. 269-281, (2000).

(56) References Cited

OTHER PUBLICATIONS

Stevenson, C., "Characterization of Protein and Peptide Stability and Solubility in Non-Aqueous Solvents," Current Pharmaceutical Biotechnology, vol. 1, pp. 165-182, (2000).

Tobe, T. et al., "Targeted Disruption of the FGF2 Gene Does Not Prevent Choroidal Neovascularization in the Murine Model," American Journal of Pathology., vol. 153, No. 5, pp. 1641-1646, (1998).

Toma, H. et al., "Improved assessment of laser-induced choroidal neovascularization," Microvasc. Res., vol. 80, No. 3, pp. 295-302, (2010).

Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans, (2017).

Ujiie, H. et al., "Successful Treatment of Nail Lichen Planus with Topical Tacrolimus", Department of Dermatology, 2 pages, (2009).

Wegewitz, U. et al., "Novel Approaches in the Treatment of Angiogenic Eye Disease," Current Pharmaceutical Design, vol. 11, No. 18, pp. 2311-2330, (2005), Abstract Only.

Wu, Y. et al., "Tetramethylpyrazine (TMP) ameliorates corneal neovascularization via regulating cell infiltration into cornea after alkali burn," Biomedicine and Pharmacotherapy, vol. 109, pp. 1041-1051, (2018).

Xu, H. et al., "A Clinical Grading System for Retinal Inflammation in the Chronic Model of Experimental Autoimmune Uveoretinitis Using Digital Fundus Images," Experimental Eye Research, vol. 87, No. 4, pp. 319-326, (2008).

Yazu, H. et al., "The efficacy of 0.1% tacrolimus ophthalmic suspension in the treatment of severe atopic keratoconjunctivitis," Annals of allergy, asthma & immunology, vol. 122, No. 4, pp. 387-392 (2019).

Zakeri, M. et al., "Topical calcipotriol therapy in nail psoriasis", A study of 24 cases, Dermatology Online Journal, vol. 11, No. 3, (2005).

Zeng, Y., "Atlas of Clinical Keratoconjunctival Disease," Hubei Science and Technology Press, p. 287-299, (2011).

Zeng, Y., "Atlas of Clinical Keratoconjunctival Disease," Hubei Science and Technology Press, p. 287-299, (2011), English Translation.

Zhang, W. et al., "FK506 alleviates blood-retinal barrier breakdown and reduces retinal vascular permeability in early streptozotocin-induced diabetic rat," Int J Clin Exp Med, vol. 10, No. 9, pp. 13272-13280, (2017).

Zhang, X. et al., "Dry Eye Management: Targeting the Ocular Surface Microenvironment," International Journal of Molecular Sciences, vol. 18, p. 1398, 28 pages, (2017).

"Topical drug dosage forms for eye conditions," The Pharmaceutical Journal, (Pharmaceutical Press, May 31, 2017), available at https://pharmaceutical-journal.com/article/Id/topical-drug-dosage-forms-for-eye-conditions.

Aihara, M., "Clinical appraisal of tafluprost in the reduction of elevated intraocular pressure (IOP) in open-angle glaucoma and ocular hypertension," Clinical Ophthalmology, vol. 4, pp. 163-170, (2010).

Eva M. del Amo, "Topical ophthalmic administration: Can a drug instilled onto the ocular surface exert an effect at the back of the eye?" Frontiers in Drug Discovery 2:954771 (Sep. 8, 2022), available at https://www.frontiersin.org/articles/10.3389/fddev.2022.954771/full.

Majumdar, S., et al. "A Low Concentration of Tacrolimus/ Semifluorinated Alkane ( SFA) Eyedrop Suppresses Intraocular Inflammation in Experimental Models of Uveitis," Current Molecular Medicine, vol. 17, No. 3, pp. 211-220, (2017).

\* cited by examiner

SEMIFLUORINATED COMPOUNDS AND
THEIR COMPOSITIONS

CROSS REFERENCE TO RELATED APPLICATION

The present application is a continuation of U.S. application Ser. No. 16/874,617, filed May 14, 2020, which is a division of U.S. application Ser. No. 16/180,994, filed Nov. 5, 2018, which is a continuation of U.S. application Ser. No. 15/280,306 filed Sep. 29, 2016, which claims priority to European Patent Application Nos. 15187767.7 filed Sep. 30, 2015, and 15192441.2 filed Oct. 30, 2015, each of which are incorporated by references in their entireties.

DESCRIPTION

Field

The present invention is in the field of compositions comprising semifluorinated compounds and their use in ophthalmic administration.

Background

Semifluorinated alkanes are compounds composed of at least one non-fluorinated hydrocarbon segment and at least one perfluorinated hydrocarbon segment. Linear, unbranched semifluorinated alkanes of the general formula $CF_3(CF_2)_n(CH_2)_mCH_3$, wherein n and m are integers denoting the number of carbon atoms of the respective segment are described for various applications, for example commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery.

Semifluorinated alkanes of the formula $CF_3(CF_2)_n(CH_2)_mCH_3$ are described in other applications.

WO 2011/073134 discloses solutions of ciclosporin in a semifluorinated alkanes of the formula $CF_3(CF_2)_n(CH_2)_mCH_3$, optionally in the presence of a co-solvent such as ethanol, wherein the semifluorinated alkane functions as a liquid drug delivery vehicle for ciclosporin for topical treatment of keratoconjunctivitis sicca. WO2014/041055 describes mixtures of semifluorinated alkanes of the formula $CF_3(CF_2)_n(CH_2)_mCH_3$ (which may be alternatively expressed as $F(CF_2)_n(CH_2)_mH$). These mixtures are described to be ophthalmically applicable as tear film substitutes or for treating patients with dry eye syndrome and/or meibomian gland dysfunction.

A nomenclature which is frequently used for semifluorinated compounds having linear and unbranched segments is FnHm, wherein F means a perfluorinated hydrocarbon segment, H means a non-fluorinated segment, and n and m define the number of carbon atoms of the respective segment. For example, F3H3 is used for perfluoropropylpropane, $CF_3(CF_2)_2(CH_2)_2CH_3$, i.e. 1-perfluoropropylpropane.

Semifluorinated alkanes of formula $CF_3—(CF_2)_5—CH(CH_3)—(CH_2)_5—CH_3$ and compositions comprising $CF_3(CF_2)_5(CH_2)_7CH_3$ and $CF_3—(CF_2)_5—CH(CH_3)—(CH_2)_5—CH_3$ however have not been described, in particular for ophthalmic applications. It is therefore an object of the invention to provide compositions comprising such compounds, in particular in respect of their use in compositions for use in ophthalmic applications.

SUMMARY OF THE INVENTION

In a first aspect, the invention relates to a composition comprising $CF_3(CF_2)_5(CH_2)_7CH_3$ and $CF_3—(CF_2)_5—CH(CH_3)—(CH_2)_5—CH_3$. In particular, the invention relates to such compositions, comprising at least about 80 wt % of $CF_3(CF_2)_5(CH_2)_7CH_3$, and in another aspect, to such compositions comprising up to about 25 wt % of $CF_3—(CF_2)_5—CH(CH_3)—(CH_2)_5—CH_3$.

In another aspect, the present invention relates to compositions comprising said compounds in the form of clear, liquid solutions.

In still another aspect the invention provides the use of composition comprising $CF_3(CF_2)_5(CH_2)_7CH_3$ and $CF_3—(CF_2)_5—CH(CH_3)—(CH_2)_5—CH_3$ for treatment of dry eye disease and/or Meibomian Gland Dysfunction and any symptoms or conditions associated with these conditions.

In a further aspect, the present invention provides a method for treatment of dry eye disease and/or Meibomian Gland Dysfunction and any symptoms or conditions associated thereof comprising administering said composition topically to the lacrimal sac, into the lower eyelid, to an eye surface or to an ophthalmic tissue.

In a yet further aspect, the present invention provides a kit comprising compositions of the present invention held in a container which comprises dispensing means adapted for topical administration of the composition to the eye or ophthalmic tissue.

DETAILED DESCRIPTION OF THE INVENTION

In a first aspect, the invention relates to a composition comprising $CF_3(CF_2)_5(CH_2)_7CH_3$ and $CF_3—(CF_2)_5—CH(CH_3)—(CH_2)_5—CH_3$.

The compound $CF_3—(CF_2)_5—CH(CH_3)—(CH_2)_5—CH_3$ may also be referred to as 2-perfluorohexyloctane, based on the hydrocarbon alkane as the root. This compound features a stereocenter at the 2-alkyl position. As understood herein, the general formula encompasses both enantiomers, enriched mixtures of the two enantiomers, as well as the racemic mixture. The compound $CF_3(CF_2)_5(CH_2)_7CH_3$ may alternatively be referred to as 1-perfluorohexyloctane, or F6H8, following the nomenclature FnHm, wherein n is an integer representing the number of carbon atoms of the linear, unbranched perfluorinated segment and m is an integer representing the number of carbon atoms of the linear, unbranched hydrocarbon segment.

Particularly preferred compositions of the invention are those that comprise at least about 80 wt % of $CF_3(CF_2)_5(CH_2)_7CH_3$. In other embodiments, the compositions comprise of at least about 90 wt % or at least about 95 wt % or at least 97 wt % of $CF_3(CF_2)_5(CH_2)_7CH_3$. In another preferred embodiment of the invention, the compositions comprise up to about 25 wt % of $CF_3—(CF_2)_5—CH(CH_3)—(CH_2)_5—CH_3$. In other embodiments, the compositions comprise up to about 10 wt %, or up to about 5 wt % or up to about 3 wt % of the compound $CF_3—(CF_2)_5—CH(CH_3)—(CH_2)_5—CH_3$.

As used herein, the term wt % refers to the weight of a component as a percentage fraction of the weight of the composition determined as a whole. The term about preceding a parameter such as wt % includes the precise value as well as any value falling within the degree of variability usually observed in the measurement and determination of the parameter, including standard techniques and equipment known in the art and field.

In a further preferred embodiment, the compositions of the invention comprising of about 97 wt % of $CF_3(CF_2)_5(CH_2)_7CH_3$ and up to about 3 wt % of $CF_3—(CF_2)_5—CH(CH_3)—(CH_2)_5—CH_3$. In yet a further embodiment, the composition may comprise of about 98 wt % of $CF_3(CF_2)_5(CH_2)_7CH_3$ and up to about 1 wt % of $CF_3—(CF_2)_5—CH(CH_3)—(CH_2)_5—CH_3$.

The compositions comprising these semifluorinated alkanes as defined above are preferably in the liquid form, and are preferably formulated to be administered as a clear liquid solution. In this context, clear means the absence of dispersed solid or liquid particles which cause turbidity. In other words, such clear solution is a purely monophasic liquid system, except that minor and technically irrelevant amounts of particulate impurities may be present.

In optional embodiments, the compositions may be formulated to be administered as a gel, suspension, microemulsion, or a spray. Preferably, the compositions are provided in sterile form.

Moreover, the composition is preferably formulated as a liquid solution which exhibits a refractive index that is close to that of water which is 1.333 at room temperature (RT). In a particularly preferred embodiment, the refractive index of the liquid solutions is in the range of from about 1.30 to about 1.35 at 20° C., as determined by refractometer.

The compositions as defined above may also comprise further excipients as required or as useful such as one or more acids, bases, electrolytes, buffers, solutes, antioxidants, stabilizers, and if required, preservatives. In one preferred embodiment, the compositions as described herein are substantially free of water and/or substantially free of a preservative, such as benzalkonium chloride.

In another embodiment of the present invention, the composition as described above is substantially free of the following: (a) a polymer (b) a perfluorinated compound, and/or (c) a dissolved pharmacologically active ingredient which is not a semifluorinated alkane. Such compositions are also preferably formulated as clear liquid solutions. In another embodiment, the composition as described in any of the embodiments herein may be substantially free of a pharmacologically active ingredient, in any form and which is not a semifluorinated alkane.

As understood herein, the term 'substantially free' in reference to a composition constituent refers to the presence of said constituent in no more than trace amounts and that if present in trace amounts the constituent provides no technical contribution to the composition.

Examples of polymers which are preferably absent in the compositions of the invention include silicone polymers (polymerized siloxanes), polyether polymers and fluorinated or perfluorinated derivatives thereof.

Examples of perfluorinated compounds, i.e. compounds in which all the hydrogen atoms are replaced with fluorine, and which are preferably absent in the compositions of the invention include perfluoroalkanes such as perfluorodecalin, as well as halogenated perfluoroalkanes such as perfluorooctylbromide.

The compositions of the invention are also substantially free of a dissolved pharmacological active ingredient which is not a semifluorinated alkane; as used herein, the term "pharmacological active ingredient" refers to any type of pharmaceutically active compound or drug, i.e. one that produces a pharmacological effect and that may accordingly be useful in the prevention, diagnosis, stabilization, treatment, or generally speaking, the management of a condition or disease.

In a preferred embodiment, the composition according to the present invention essentially consists of $CF_3(CF_2)_5(CH_2)_7CH_3$ and $CF_3—(CF_2)_5—CH(CH_3)—(CH_2)_5—CH_3$. Preferably the composition essentially consists of about 97 wt % of $CF_3(CF_2)_5(CH_2)_7CH_3$ and up to about 3 wt % of $CF_3—(CF_2)_5—CH(CH_3)—(CH_2)_5—CH_3$.

As used herein, the term "essentially consisting of" is so-called closed language, meaning that only the mentioned constituents are present. In contrast, the terms "comprise", "comprises" and "comprising" are used herein as so-called open language, meaning that further constituents may also be present.

The compounds of the invention as well as the compositions comprising these, even if free of other pharmacologically active ingredients, however have beneficial therapeutic effects at the site of administration.

The compositions as defined above are preferably formulated to have a dynamic viscosity of not more than 10 mPa·s, and preferably not more than 4 mPa·s, as determined under standard ambient temperature and pressure (25° C., 1 atm). Preferably, the compositions have a dynamic viscosity of between 1 and 4 mPa·s. The viscosity of the compositions may be determined using any standard viscometer device known in the art, such as a glass tube or capillary viscometer.

The compositions as described herein may be used in medical applications, in particular for use in ophthalmology, and in particular in the topical administration to the eye, such as to the lacrimal sac, into the lower eyelid, to an eye surface or to any ophthalmic tissue or anatomy associated with the eye that may be made available for topical administration.

It has been found that the compositions of the invention are beneficial for use in the treatment of diseases and conditions which would benefit from stabilization of the tear film and tear film lipid layer and lubrication of the eye surface. Thus, the compositions of the present invention are especially suited in the treatment of dry eye disease (keratoconjunctivitis sicca) and/or Meibomian Gland Dysfunction (MGD) and any symptoms thereof or associated therewith.

Dry eye disease, also known as keratoconjunctivitis sicca, can be distinguished into two categories, namely aqueous deficient dry eye disease and evaporative dry eye disease. These conditions are not necessarily mutually exclusive. Aqueous deficient dry eye is typically observed in patients suffering from Sjögren syndrome, or those suffering from a lacrimal gland insufficiency, lacrimal duct obstruction or reflex hyposecretion. Evaporative dry eye disease on the other hand has diverse root causes and is associated with increased/abnormal evaporative loss of the tear film, for example as a result of meibomian gland disorders, eyelid aperture disorders, blinking disorders, or ocular surface disorders.

Symptoms of dry eye disease include dry, scratchy, gritty, sandy or foreign body sensations in the eye; pain, soreness, stinging or burning; itching, increased need for blinking, eye fatigue, photophobia, blurry vision, redness and inflammation of the eye tissue, excess mucus discharge and crusting/clotting, contact lens intolerance, and excess reflex tearing.

Meibomian Gland Dysfunction (MGD) refers to a condition where the meibomian glands do not secrete enough oil or when the oily secretions are of poor or abnormal quality. Often, the oil gland openings may become plugged up or obstructed so that less oil is secreted from the glands. The oil is secreted from the glands can be granular (crusty) or otherwise abnormal, and can cause irritation to the eye and eye tissues. In the early stages, patients are often asymptomatic, but if left untreated, MGD can cause or exacerbate dry eye symptoms and eyelid inflammation. The oil glands become blocked with thickened secretions. Chronically clogged glands eventually become unable to secrete oil, which may result in permanent changes in the tear film and dry eyes.

Symptoms of Meibomian Gland Dysfunction include dryness, burning, itching, stickiness/crustiness, watering light sensitivity, red eyes, foreign body sensation, chalazion/styes or intermittent blurry vision.

In a preferred embodiment, the compositions of the invention as described above are used for the topical ophthalmic treatment of evaporative dry eye disease and or Meibomian Gland Dysfunction (MGD), and for the treatment or prevention of any one of the symptoms or conditions associated thereof. In another embodiment, the compositions as described herein may be used as a lubricant of the eye surface, so as to ameliorate one or more of the symptoms associated with dry eye disease and to wet the eye surface.

In another preferred embodiment of the invention, the compounds and compositions thereof as described above are used for the topical ophthalmic treatment of corneal damage. Thus, said compounds and compositions are actively supporting the corneal healing process of corneal damage, such as corneal erosions.

In further embodiments, the treatment of the above described conditions (e.g. corneal damage) and diseases, and their associated symptoms, also as described above is preferably carried out by a method of administering to a patient in need thereof, an effective amount of a composition as described above, comprising $CF_3(CF_2)_5(CH_2)_7CH_3$ and $CF_3—(CF_2)_5—CH(CH_3)—(CH_2)_5—CH_3$, for example wherein the composition comprises up to about 25 wt % of $CF_3—(CF_2)_5—CH(CH_3)—(CH_2)_5—CH_3$.

The advantages of the compounds and compositions described above in the context of their use according to the present invention, are believed to relate to their properties which are particularly suited for ophthalmic applications. The close proximity of the refractive indices of the compounds of the invention to that of water, means that there would be no or minimal impact of a patient's vision subsequent to administration, unlike ophthalmic compositions based on oily carriers which can confer blurry vision on administration. The generally low viscosity and low surface tension and in particular their high wetting and spreading capabilities of these compounds also ensures that they are rapidly accommodated and adapted on administration over the surface of the eye.

As will be made clearer in the examples below, it was found that the compositions of the invention are biocompatible and exhibit no apparent cytotoxic effects. Moreover, it has been established that these compositions are not only well tolerated in the eye and has no impact on visual acuity, but also provide a beneficial effect in terms of lubrication of the eye and stabilization of the tear film, in the form of relief in symptoms of patients having mild to moderate symptoms associated with dry eye disease. Patients with dry eye disease and/or dysfunctional meibomian glands often express opaque and thicker meibum which can lead to an abnormal lipid layer in the tear film. Without wishing to be bound to theory, it is believed that the physico-chemical attributes of the compounds featured in the compositions of the invention may play a role in stabilizing the lipid layer of the tear film, such as by solubilization of certain lipid components or improving the fluidity of the lipid layer, as well as provide a lubricating effect on the eye In a further aspect, the present invention provides a method for treatment of dry eye disease and any symptoms or conditions associated thereof comprising administering the compositions of the present invention topically to the lacrimal sac, into the lower eyelid, to an eye surface or to an ophthalmic tissue. Preferably, said compositions can be administered to the eye or eye tissue up to four times per day.

Furthermore, the invention provides for a kit comprising any one of the compositions as described above, and a container for holding said composition. Said container preferably comprises a dispensing means adapted for topical administration of the composition to an eye sac, lower eyelid to an eye or ophthalmic tissue, such as an eye dropper.

In a further preferred embodiment, the dispensing means comprises a dropper of dimensions such as to dispense droplets having a volume of 8 to 15 µL, preferably of about 8-12 µl, more preferably of about 10 µl. With a small droplet volume, precise dosing to the eye can be achieved and an excess amount of discharge of a substantial fraction of the composition from the eye subsequent to administration can be avoided.

The compositions of the invention moreover can be administered to the eye or eye tissue up to four times per day; preferably with one drop (ca. between 8 to 15 µL in volume) administered per eye, and per dose. Treatment may last up to at least six weeks. In one embodiment of the invention, the compositions is administered at a dose of 1 drop of about between 8 to 15 µL volume, preferably of about 10 µl volume to each eye three to four times per day.

EXAMPLES

Preparation of $CF_3—(CF_2)_5—CH(CH_3)—(CH_2)_5—CH_3$ (2-Perfluorohexyl-octane. $C_{14}F_{13}H_{17}$)

The compound $CF_3—(CF_2)_5—CH(CH_3)—(CH_2)_5—CH_3$ may be prepared as follows: radical addition of perfluorohexyl iodide with 1-octene in the presence of a radical initiator (herein perfluorohexyl iodide is mixed with 1-octene and a radical initiator as AIBN and the obtained solution is maintained at 80° C. for 30 min and cooled down), followed by reduction of the resulting iodo adduct with hydride (i.e. LiALH4) or via hydrogenation (i.e. catalytic hydrogenation in presence of a catalyst such as Pd/C) to form 2-perfluorohexyl-octane, followed by purification by fractional distillation.

$CF_3$—$(CF_2)_5$—$CH(CH_3)$—$(CH_2)_5$—$CH_3$. $^1$H-NMR (CDCl3, 400 MHz): 2.17-2.33 (m, 1H, CH), 1.67-1.77 (m, 2H, $CH_2$), 1.25-1.40 (m, 8H, $CH_2$), 1.15 (d, 3H, $CH_3$), 0.9 (t, 3H, $CH_3$)

In Vitro Cytotoxicity Assay

The cytotoxicity of a composition comprising 1.3 wt % $CF_3$—$(CF_2)_5$—$CH(CH_3)$—$(CH_2)_5$—$CH_3$ and 95.8 wt % $CF_3(CF_2)_5(CH_2)_7CH_3$ was assessed by a cell growth inhibition test which predicts cytotoxic or necrotic effects with good correlation to animal experiments and high sensitivity.

The composition was extracted by cell culture medium (DMEM supplemented with 10% FBS) under agitation for ~24 hours. The resulting extract was then incubated with mouse cell line L929 cells for 68-72 hours, before the protein content was analyzed using a BCA (bicinchoninic acid) test as a measure for cytotoxicity. No inhibition of cell growth or cell lysis was observed.

An analogous in vitro cytotoxicity assay is conducted for a composition comprising about 23.7 wt % $CF_3$—$(CF_2)_5$—$CH(CH_3)$—$(CH_2)_5$—$CH_3$ and about 75.6 wt % F6H8.

Tear Film Analysis Studies

A composition comprising 98.3 wt % of $CF_3(CF_2)_5(CH_2)_7CH_3$ and 1.2 wt % of $CF_3$—$(CF_2)_5$—$CH(CH_3)$—$(CH_2)_5$—$CH_3$ was tested in an observational study in patients with mild to moderate evaporative dry eye disease. The clear colorless liquid composition was provided in a 5 ml bottle equipped with a dropper dimensioned to dispense of droplets of ~10 μl per drop into the eye sac. Patients wearing contact lenses were excluded from the study. After informed consent had been obtained, patients were advised to apply 3-4 drops, daily in both eyes, translating to a daily dose of 30-40 μl. Patients returned after 5-7 weeks for follow-up. Clinical data for 29 patients were collected at baseline and at the 5-7 week follow-up visit.

a) Tear Film Analysis

Tear film fluid and tear film stability improved over the study period, as can be seen in the increase in Schirmer I and the TFBUT. The retrospective statistical analysis is strengthening this observation, as the difference in TFBUT at baseline and follow-up is highly significant (paired two-sided t-test: p=0.0026 (right eyes) and p=0.0006 (left eyes)). No changes were detected in tear osmolarity.

The subjective dry eye questionnaire (Ocular Surface Disease Index, OSDI) revealed that patient's subjective symptom severity decreased after the use of the composition comprising 98.3 wt % of $CF_3(CF_2)_5(CH_2)_7CH_3$ and 1.2 wt % of $CF_3$—$(CF_2)_5$—$CH(CH_3)$—$(CH_2)_5$—$CH_3$ over a 5-7 week period, as can be seen in the lower scores at follow-up and the retrospective statistical analysis (paired two sided t-test: p<0.0001).

| Parameter | Baseline | Follow up |
|---|---|---|
| Schirmer I (mm/5 min)/Right eye | 10.7 ± 3.7 | 16.3 ± 8.9 |
| TFBUT (sec) | Right eye: 5.7 ± 2.6 | Right eye: 7.9 ± 5.1 |
| | Left eye: 5.7 ± 2.6 | Left eye: 8.6 ± 6.0 |
| Osmolarity | 315.7 ± 12.8 | 311.4 ± 14.7 |
| OSDI | 53.9 ± 22.5 | 35.8 ± 22.9 | b) Corneal Staining (Oxford Grading Scheme)

Corneal fluorescein staining is an indicator of corneal damage (loss of cell-to-cell junctions). The data indicate a reduction of corneal damage after 5-7 weeks of treatment, as can be seen in the shift of numbers of patients diagnosed with Grade 1 or 2 at baseline towards Grade 0 at follow-up. This difference to the initial level of damage was statistically significant, as shown by Wilcoxon signed rank test: p=0.0013 (right eyes) and p=0.0041 (left eyes).

| | Baseline (n = 29) | | | Follow up (n = 28) | | |
|---|---|---|---|---|---|---|
| | Grade 0 | Grade 1 | Grade 2 | Grade 0 | Grade 1 | Grade 2 |
| Right eye (n) | 8 (1) | 16 | 4 | 25 | 2 | 1 |
| Left eye (n) | 8 (1) | 16 | 4 | 19 | 9 | 0 | c) Symptom Assessment by Physician

Patients were asked by the physician whether they currently suffer from typical dry eye symptoms both at the baseline and at the follow-up visit. As can be seen in the table below, a lower number of DED-associated symptoms were reported after 5-7 weeks of treatment.

| | Baseline | Follow up |
|---|---|---|
| Red eyes | 25 | 9 |
| Itching | 21 | 10 |
| Clotted eyes | 9 | 2 |
| Stringy mucous | 4 | 1 |
| Headache | 2 | 1 | d) Meibum Secretion analysis

In a healthy eye, meibum is secreted from the meibomian glands as a clear liquid. More opaque and thicker meibum is an indicator of dysfunctioning meibomian glands. Patients' meibum was descriptively examined at both the baseline and the follow-up visit. According to the data obtained, meibum quality improved in a number of cases. In seven cases, the treatment induced a reduction of expressible meibum (changing from clear meibum to none).

| | Baseline | Follow up |
|---|---|---|
| Clear | 20 | 17 |
| Whitish | 6 | 3 |
| Thick | 1 | 0 |
| None | 2 | 9 | e) Safety Parameters

No changes were seen in either visual acuity or intraocular pressure, indicating that the use of composition comprising 98.3 wt % of $CF_3(CF_2)_5(CH_2)_7CH_3$ and 1.2 wt-% of $CF_3$—$(CF_2)_5$—$CH(CH_3)$—$(CH_2)_5$—$CH_3$ over 5-7 weeks is safe and does not interfere with these ophthalmological parameters.

| | Baseline | Follow up |
|---|---|---|
| Visual acuity | 0.8 (0.7-1.0) | 0.9 (0.8-1.0) |
| Intraocular pressure (mm HG) | 14.9 ± 2.6 | 14.6 ± 3.2 |

Differential Scanning Calorimetry

Differential Scanning calorimetry (DSC 1, Mettler Toledo, Greifensee, Switzerland) is used to characterize structure and phase behavior of mixtures of $CF_3(CF_2)_5$—$CH(CH_3)$—$(CH_2)_5$—$CH_3$ and $CF_3(CF_2)_5(CH_2)_7CH_3$. DSC was employed to obtain data on transitions by temperature rising scans with heating rate of 1° C./min. Sealed standard aluminum crucibles (40 μl, Mettler Toledo) were used.

| wt % | Melting transition | | | |
|---|---|---|---|---|
| $CF_3$—$(CF_2)_5$—$CH(CH_3)$—$(CH_2)_5$—$CH_3$ | ΔH (J/g) | Onset (° C.) | Peak (° C.) | Endset (° C.) |
| 0 | −36.57 | −6.33 | −4.53 | −2.14 |
| 5.91 | −33.36 | −10.32 | −7.99 | −7.24 |
| 12.03 | −29.42 | −13.74 | −10.44 | −9.58 |
| 23.74 | −24.09 | −21.56 | −15.38 | −14.17 |

| wt % | Low temperature transition | | | |
|---|---|---|---|---|
| $CF_3(CF_2)_5$—$CH(CH_3)$—$(CH_2)_5$—$CH_3$ | ΔH (J/g) | Onset (° C.) | Peak (° C.) | Endset (° C.) |
| 0 | −0.69 | −45.47 | −40.37 | −38.32 |
| 5.91 | −0.56 | −50.61 | −45.77 | −42.93 |
| 12.03 | −0.44 | −55.18 | −48.58 | −45.53 |
| 23.74 | −0.19 | −60.75 | −54.39 | −52 |

The presence of $CF_3(CF_2)_5$—$CH(CH_3)$—$(CH_2)_5$—$CH_3$ in a mixture of $CF_3(CF_2)_5$—$(CH_2)_7$—$CH_3$ (F6H8) resulted in a significant reduction in the melting temperature. The melting enthalpy is also decreased, which suggests that this semifluorinated alkane does not crystallize. Such differences will have a beneficial effect in respect of the application of this compound to the eye as a tear film substitute or lubricant; for example, in terms of its ability to mix with, and to modulate the tear film lipid layer. Such effects can moreover be advantageously tuned by varying the amounts of this compound in the ophthalmic compositions of the invention.

DSC measurements of a series of mixtures of 23.74 wt % of $CF_3(CF_2)_5$—$CH(CH_3)$—$(CH_2)_5$—$CH_3$ and $CF_3(CF_2)_5(CH_2)_7CH_3$ with tetradecane (C14) was also performed. Data on transitions were obtained with temperature rising scans (heating rates 0.2, 0.5 and 1° C./min). Extrapolation to a heating rate of 0° C./min was used to determine endset temperatures while average from the three measurements were used to determine onset temperatures. A decrease in the melting enthalpy was observed, compared to mixtures of tetradecane with pure $CF_3(CF_2)_5(CH_2)_7CH_3$, suggesting that some of the tetradecane is dissolved in the liquid fraction of $CF_3(CF_2)_5$—$CH(CH_3)$—$(CH_2)_5$—$CH_3$ and that this compound has a stronger solubilizing capacity compared to $CF_3(CF_2)_5(CH_2)_7CH_3$.

Refractive Index and Evaporation Time

The evaporation time of mixtures of the semifluorinated alkane $CF_3(CF_2)_5(CH_2)_7CH_3$ and $CF_3(CF_2)_5$—$CH(CH_3)$—$(CH_2)_5$—$CH_3$ was evaluated. A droplet of 10 μL volume of each mixture was placed on a glass surface at room temperature. Time until evaporation was recorded by videomonitoring.

Figure 2:
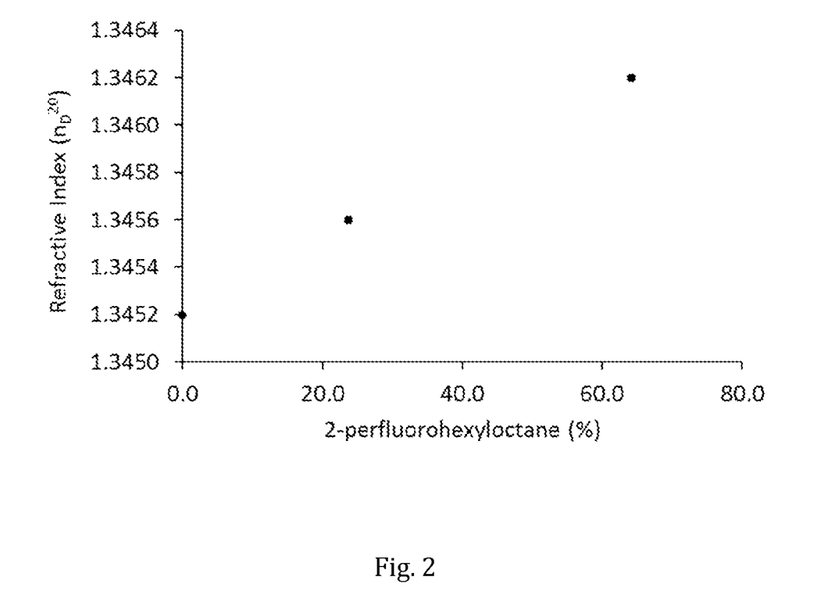
FIG. 2 is a graph depicting the refractive index determined for compositions consisting of the compounds $CF_3(CF_2)_5(CH_2)_7CH_3$ and $CF_3—(CF_2)_5—CH(CH_3)—(CH_2)_5—CH_3$ as a function of the percentage of the latter compound in the composition.

The refractive index of the mixtures was also determined. For topically applied ophthalmic compositions, the refractive index of the composition should preferably similar, or adapted to that of the eye and lens, for instance as close to that of physiological tear fluid as possible. If the refractive index of a composition is not similar, when applied to the surface of the eye, a patient may experience blurring or impaired vision. It is observed, that the amount of the semifluorinated alkane $CF_3(CF_2)_5$—$CH(CH_3)$—$(CH_2)_5$—$CH_3$ has an effect on refractive index (see FIG. 2, which depicts an increasing refractive index value with increased content of the 2-perfluorohexyloctane). By varying the amount of this semifluorinated alkane in the mixture, it may also be feasible to adapt the composition to the requirements of the intended ophthalmic use, for instance adapting to a patient with an altered tear fluid composition and refractive index, due to an eye condition and/or age.

Ex Vivo Eye Irritation Test (EVEIT)

A comparison in respect of corneal healing process was conducted for two compositions comprising $CF_3(CF_2)_5(CH_2)_7CH_3$, namely compositions consisting of a mixture of the semifluorinated alkane $CF_3(CF_2)_5(CH_2)_7CH_3$ and $CF_3(CF_2)_5$—$CH(CH_3)$—$(CH_2)_5$—$CH_3$ (Composition A with 0.17 wt % of $CF_3(CF_2)_5$—$CH(CH_3)$—$(CH_2)_5$—$CH_3$ and Composition B, with 64 wt % of $CF_3(CF_2)_5$—$CH(CH_3)$—$(CH_2)_5$—$CH_3$) with hyaluronic acid (HYLO-COMOD®) as a reference and 0.01% BAC (benzalkonium chloride) as a positive control using an Ex Vivo Eye Irritation Test (EVEIT), similar to as described in M. Frentz et al, Altern. to Lab. Anim., 2008 (36) p 25-32; and N. Schrage et al, Graefes Arch Clin Exp Ophthalmol 2012 (250), 1330-1340).

| Sample | $CF_3(CF_2)_5(CH_2)_7CH_3$/% | $CF_3(CF_2)_5$—$CH(CH_3)$—$(CH_2)_5$—$CH_3$/% | Evaporation time/s | Relative Evaporation Time |
|---|---|---|---|---|
| 1 | 99.84 | 0.16 | 13260 | 1 |
| 2 | 96.53 | 3.05 | 12960 | 0.97 |
| 3 | 26.3 | 64.1 | 9960 | 0.75 |

Figure 1:
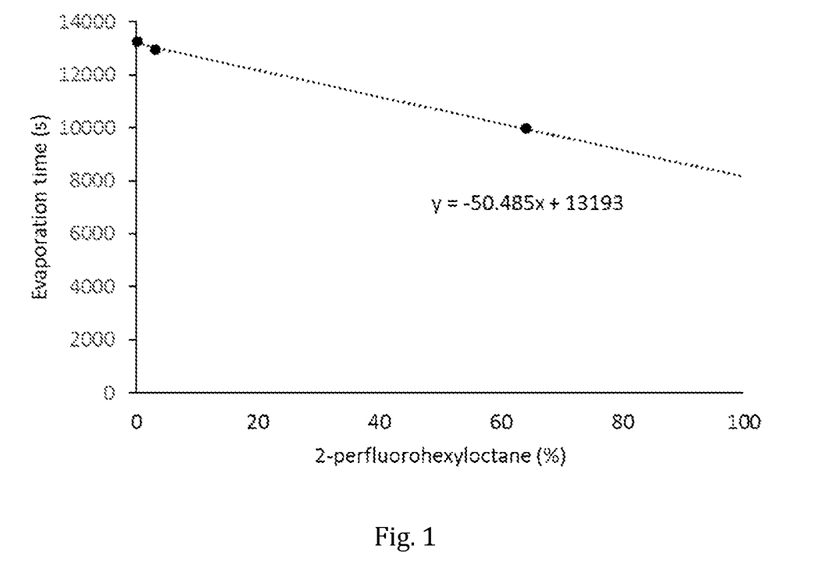
FIG. 1 is a graph depicting the evaporation time of compositions consisting of the compounds $CF_3(CF_2)_5(CH_2)_7CH_3$ and $CF_3—(CF_2)_5—CH(CH_3)—(CH_2)_5—CH_3$ as a function of the percentage of the latter compound in the composition.

It was observed that an increasing percentage of the semifluorinated alkane $CF_3(CF_2)_5$—$CH(CH_3)$—$(CH_2)_5$—$CH_3$ decreases the evaporation time of the mixtures (FIG. 1) By varying the amount of this semifluorinated alkane in the mixture, it may feasible to adapt and fine-tune the composition to the requirements of the intended ophthalmic use, such as in terms of prolonging or reducing the residence time of the composition on the eye surface.

Method. Rabbit corneas were obtained and placed in an artificial anterior ocular chamber which was gently filled with serum-free minimal essential medium (Eagle's MEM) containing Earle's salts and HEPES buffer for nutrition. The medium was contstantly replenished by a micropump to imitate the physiological condition of the eye. The culture chambers were held at 32° C. under normal air without supplementary $CO_2$ and >95% relative humidity. Five corneas per test substance (n=5) were used except for the postive control with which two corneas (n=2) were tested.

After 12 h of stabilization in the culture chamber, the corneas were evaluated by microscopy and corneas with intact epithelium and without opacities were selected. Four small abrasions (2.3-4.3 mm$^2$) were applied to the surface of the selected corneas with a cornea drill. All defects were monitored by fluorescein sodium staining (0.17% aq. solution) and microscopy.

The test substances were administered one hour after induction of the corneal erosion and were applied six times daily onto the apex of the corneas (30-50 μL every four hours). A soft-tipped cannula, with continuous suction was placed on the lowest part of the corneoscleral region within the culturing chamber to remove any excess fluid. Experiments were terminated after 3 days of application. Biomicroscopic images of the corneas were taken daily to document the corneal healing process using a phase-contrast microscope integrated camera (KY-F1030U, JVC, (Bad Vilbel, DE) mounted on a Z16 APO Microscope (Wetzlar, DE)). All defects were monitored by fluorescein sodium stains (0.17% aq. solution) with yellow green fluorescence indicating the areas of epithelial defects. Erosion sizes were determined using a software tool of the microscope (DISKUS). At the end of the 3 days, the experiment was terminated and all corneas were fixed in 3.7% formaldehyde and stained with a hematoxylin-eosin dye for microscopic evaluation. To monitor the metabolic activity of the cornea, glucose and lactate concentrations were photometrically quantified in the outflow medium from the artificial anterior chambers.

Results. Both mixtures of the semifluorinated alkanes (Composition A and B as referenced above) were observed to have a similar positive effect in respect of the corneal healing process after the induction of corneal erosion as compared with the standard reference hyaluronic acid composition (HYLO-COMOD®).

Corneal Erosion Size Measurements/Mean mm$^2$ (SD)

| Composition | Day 0 | Day 1 | Day 2 | Day 3 |
| --- | --- | --- | --- | --- |
| A (n = 5) | 12.8 (0.98) | 3.018 (0.89) | 0 (0) | 0 (0) |
| B (n = 5) | 12.23 (1.46) | 3.59 (0.53) | 0 (0) | 0 (0) |
| HYLO COMOD ® | 12.13 (1.29) | 3.11 (0.76) | 0.01 (0.02) | 0 (0) |
| 0.01% BAC | 11.57 (0.86) | 5.91 (0.28) | 8.74 (7.6) | 17.46 (6.43) |

Day 3 Histological Observations

| Composition | |
| --- | --- |
| A (n = 5) | Multilayered epithelium and dense stroma in all corneas. Keratocytes are well formed and arranged except if lost from initial erosion area. Descemet membrane appears intact, endothelial cells are present. |
| B (n = 5) | Healed epithelial layer with closed multilayer of epithelial cells. Dense stroma and regular formed keratocytes although typically reduced in number under the initial erosion area. Descemet membrane and endothelial layer present without structural defects |
| Hylo Comod ® (reference) | Multilayered epithelium and dense stroma with regular arranged and formed keratocytes except under the initial erosion areas where keratocytes are totally lost in the upper stroma. Descemet membrane and endothelial layer are present without any defects in structure. |
| 0.01% BAC (positive control) | Severe alterations of the superficial cornea with disintegration of whole corneal structures; observation of distinct edema. Reduced staining of background substance indicating chemical alteration of collagen. Severe reduction in number of keratocyte cells which also appear rounded and pycnotic. Descemet membrane is present with intact endothelium |

Figure 3:
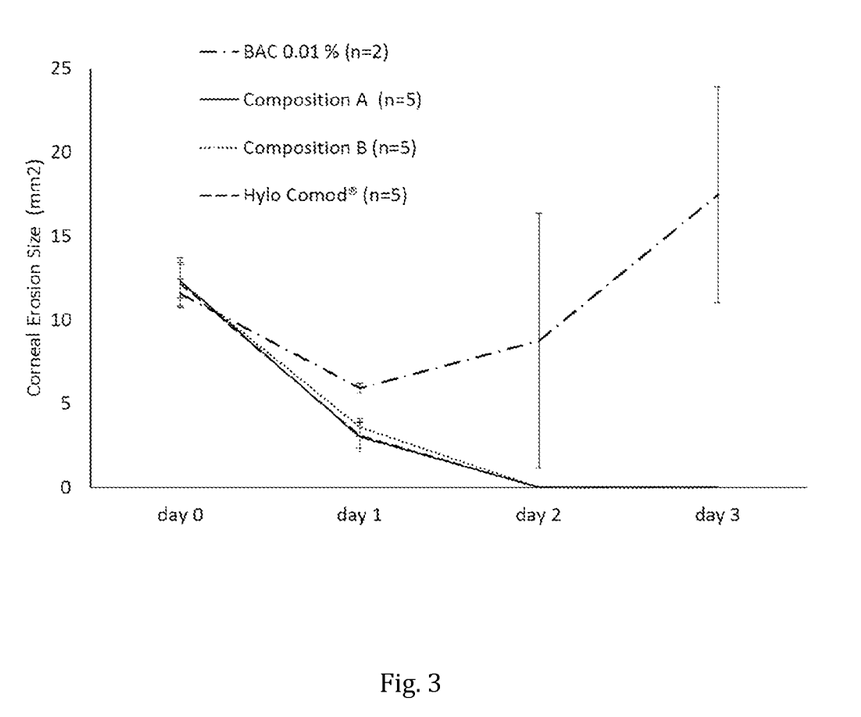
FIG. 3 is a graph representing results obtained from an Ex vivo Eye Irritation Test (EVEIT) comparison of compositions of $CF_3(CF_2)_5(CH_2)_7CH_3$ and $CF_3—(CF_2)_5—CH(CH_3)—(CH_2)_5—CH_3$, a hyaluronic standard reference and 0.01% BAC positive control.

No significant differences in terms of a positive corneal healing was noted between composition B comprising 64 wt %, based on total weight of the composition of semifluorinated alkane $CF_3(CF_2)_5$—$CH(CH_3)$—$(CH_2)_5$—$CH_3$ and composition A. With both compositions, as with the reference composition, the mechanically induced epithelial erosions were found to be significantly reduced and essentially absent after day 2 of treatment. FIG. 3 depicts the corneal erosion size measurements of the tested compositions, reference and positive controls for days 0-3 of the EVEIT experiment.

As noted in the table above, microscopic histological examination of the cross-sections of the corneas after termination of the experiment on day 3 revealed no significant remaining defects or differences in the corneas treated with compositions A, B and the reference HYLO-COMOD®.

Furthermore, no corneal toxicity, based on the metabolic activity as indicated by the glucose/lactate measurements was observed for these compositions.

In significant contrast, the positive control comprising 0.01% of the preservative BAC, a progressive increase of the induced epithelial lesions was observed over the course of the three days of the experiment.

The invention claimed is:

1. A composition comprising $CF_3(CF_2)_5(CH_2)_7CH_3$ and $CF_3$—$(CF_2)_5$—$CH(CH_3)$—$(CH_2)_5$—$CH_3$.

2. The composition according to claim 1, comprising at least about 80 wt % of $CF_3(CF_2)_5(CH_2)_7CH_3$.

3. The composition according to claim 1, comprising up to about 25 wt % of $CF_3$—$(CF_2)_5$—$CH(CH_3)$—$(CH_2)_5$—$CH_3$.

4. The composition according to claim 1, comprising about 97 wt % of $CF_3(CF_2)_5(CH_2)_7CH_3$ and up to about 3 wt % of $CF_3$—$(CF_2)_5$—$CH(CH_3)$—$(CH_2)_5$—$CH_3$.

5. The composition according to claim 1, being formulated as a clear liquid solution.

6. The composition according to claim 1, being free of:
(a) a polymer,
(b) a perfluorinated compound, and/or
(c) a dissolved pharmacologically active ingredient.

7. The composition of according to claim 1, having a dynamic viscosity of not more than 10 mPa·s, at ambient temperature and pressure.

8. The composition according to claim 1, wherein the composition has a refractive index between 1.30 and 1.35 at 20° C., as determined by a refractometer.

9. A kit comprising a composition comprising $CF_3(CF_2)_5(CH_2)_7CH_3$ and $CF_3$—$(CF_2)_5$—$CH(CH_3)$—$(CH_2)_5$—$CH_3$ and a container for holding the composition.

10. The kit of claim 9, wherein the container comprises a dispensing means adapted for topical administration of the composition to a lacrimal sac, into a lower eyelid, to an eye surface, or to an ophthalmic tissue.

11. The kit of claim 10, wherein the dispensing means comprises a dropper which dispenses droplets having a volume of 8 to 15 μL.

12. The kit of claim 10, wherein the dispensing means comprises a dropper which dispenses droplets having a volume of 8 to 12 μL.

13. The kit of claim 10, wherein the dispensing means comprises a dropper which dispenses droplets having a volume of 10 μL.

* * * * *